United States Patent
Hillebrand et al.

(10) Patent No.: US 10,851,368 B2
(45) Date of Patent: Dec. 1, 2020

(54) DEVICE AND PROCESS FOR AUTOMATED EXTRACTION OF NUCLEIC ACIDS

(71) Applicant: AJ INNUSCREEN GMBH, Berlin (DE)

(72) Inventors: Timo Hillebrand, Hoppegarten (DE); Thorsten Stroh, Berlin (DE)

(73) Assignee: AJ INNUSCREEN GMBH, Berlin (DE)

( * ) Notice: Subject to any disclaimer, the term of this patent is extended or adjusted under 35 U.S.C. 154(b) by 287 days.

(21) Appl. No.: 15/568,471

(22) PCT Filed: Feb. 26, 2016

(86) PCT No.: PCT/EP2016/054180
§ 371 (c)(1),
(2) Date: Oct. 21, 2017

(87) PCT Pub. No.: WO2016/169679
PCT Pub. Date: Oct. 27, 2016

(65) Prior Publication Data
US 2018/0148766 A1    May 31, 2018

(30) Foreign Application Priority Data

Apr. 23, 2015  (DE) .................. 10 2015 207 481
Jun. 19, 2015  (DE) .................. 10 2015 211 393
Jun. 19, 2015  (DE) .................. 10 2015 211 394

(51) Int. Cl.
| | | |
|---|---|---|
| *C12Q 1/6806* | (2018.01) | |
| *G01N 1/40* | (2006.01) | |
| *B01L 3/02* | (2006.01) | |
| *C12N 15/10* | (2006.01) | |
| *G01N 35/10* | (2006.01) | |

(52) U.S. Cl.
CPC ........ *C12N 15/1006* (2013.01); *B01L 3/0275* (2013.01); *C12N 15/1013* (2013.01);
(Continued)

(58) Field of Classification Search
CPC ....... B01L 2200/023; B01L 2200/0631; B01L 220/0647; B01L 2300/0854;
(Continued)

(56) References Cited

U.S. PATENT DOCUMENTS 6,565,728 B1 *  5/2003  Kozulic ............... B26D 7/1818
                                                      204/606
2006/0124551 A1  6/2006  Gjerde et al.
(Continued)

FOREIGN PATENT DOCUMENTS

WO        01/32310     *   5/2001

OTHER PUBLICATIONS

Vogelstein et al. "Preparative and analytical purification of DNA from agarose" Proceedings of the National Academy of Sciences, vol. 76, No. 2; pp. 615-619; Feb. 1, 1979.
(Continued)

*Primary Examiner* — Maureen Wallenhorst
(74) *Attorney, Agent, or Firm* — Grüneberg and Myers PLLC

(57) ABSTRACT

A device and method are useful for automated extraction of nucleic acids. The device can include a body that can be immersed partly or completely in a reaction cavity, where the part immersed in the reaction cavity has a non-smooth surface. After lysis, an organic substance, preferably alcohols or ketones, can be mixed with a biological sample. This mixture can be brought into contact with a material with a non-smooth surface. Under these conditions, nucleic acids may be adsorbed on the surface of the material being used. Washing steps may be carried out. After drying, the adsorbed nucleic acid may be detached from the material by adding water or a buffer of low salt concentration, whereupon it can be used for downstream applications.

6 Claims, 1 Drawing Sheet

Figure 1:
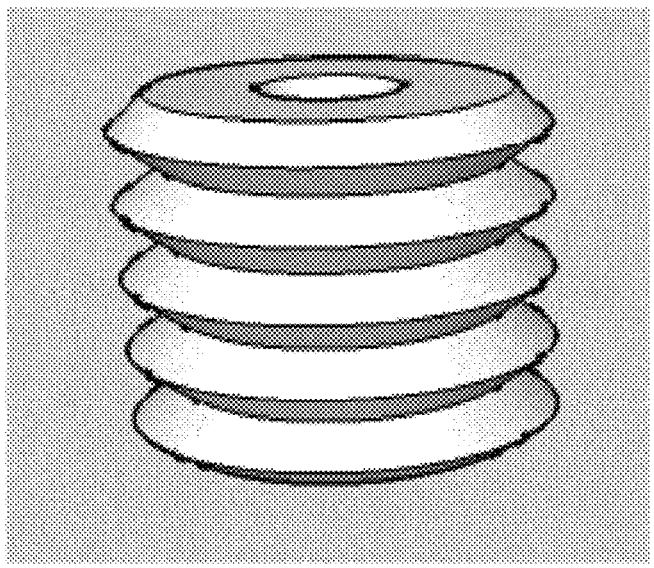

(52) U.S. Cl.
CPC ........... *C12Q 1/6806* (2013.01); *G01N 1/405* (2013.01); *G01N 35/10* (2013.01); *B01L 2200/023* (2013.01); *B01L 2200/0631* (2013.01); *B01L 2200/0647* (2013.01); *B01L 2300/0854* (2013.01); *B01L 2300/16* (2013.01); *Y10T 436/255* (2015.01); *Y10T 436/25375* (2015.01)

(58) Field of Classification Search
CPC ... B01L 2300/16; B01L 3/0275; C12N 15/10; C12N 15/1003; C12N 15/1006; C12N 15/1013; C12Q 1/6806; G01N 1/405; G01N 35/10; Y10T 436/11; Y10T 436/25; Y10T 436/25375; Y10T 436/255; Y10T 436/2575
USPC ............. 436/43, 63, 94, 174, 177, 178, 180; 422/501, 509, 510, 521, 524, 527; 435/6
See application file for complete search history.

(56) References Cited

U.S. PATENT DOCUMENTS

2007/0281303 A1\* 12/2007 Isakson ................... A01N 1/02
                                                                             435/6.16

2010/0179308 A1    7/2010  Gjerde et al.
2011/0038769 A1    2/2011  Gjerde et al.

OTHER PUBLICATIONS

Akonni: "TruTip—Breaking the speed limit on ultra-rapid nucleic acid extraction," Nov. 16, 2010; Internet citation: https://web.archive.org/web/20130917232736/http:/www.akonni.com/docs/TruTip%20Brochure.pdf.

Chandler et al.; "Rapid, simple influenza RNA extraction from nasopharyngeal samples," J. Virological Methods; vol. 183, No. 1; pp. 8-13; Mar. 1, 2012.

Holmberg et al.; "High-throughput, automated extraction of DNA and RNA from clinical samples using TruTip technology on common liquid handling robots;" Journal of Visualized Experiments, No. 76; Jun. 11, 2013.

International Search Report mailed in PCT/EP2016/054180 dated Jun. 27, 2016, with English language translation.

Written Opinion of the International Searching Authority mailed in PCT/EP2016/054180 dated Jun. 27, 2016, with English language translation.

International Preliminary Report on Patentability mailed in PCT/EP2016/054180 dated Oct. 24, 2017.

\* cited by examiner

DEVICE AND PROCESS FOR AUTOMATED EXTRACTION OF NUCLEIC ACIDS

CROSS-REFERENCE TO RELATED APPLICATIONS

This application is a National Stage entry under § 371 of International Application No. PCT/EP2016/054180 filed on Feb. 26, 2016, and claims the benefit of Germany Application Nos. 10 2015 207 481.1 filed on Apr. 23, 2015, 10 2015 211 393.0 filed on Jun. 19, 2015, and 10 2015 211 394.0 filed on Jun. 19, 2015. The content of each of these applications is hereby incorporated by reference in its entirety.

The subject matter of the invention is a device and a method with which nucleic acids can be isolated and purified rapidly and highly efficiently as well as quantitatively in an automated process.

Under traditional conditions, DNA is isolated from cells and tissues by digesting the starting materials containing nucleic acids under strongly denaturing and reducing conditions, sometimes also with use of protein-degrading enzymes, purifying the resulting nucleic acid fractions via phenol/chloroform extraction steps and obtaining the nucleic acids from the aqueous phase by means of dialysis or precipitation with ethanol (Sambrook, J., Fritsch, E. F. and Maniatis, T., 1989, CSH, "Molecular Cloning"). These "traditional methods" for isolation of nucleic acids from cells and especially from tissues are very time-consuming (sometimes longer than 48 hours), require highly complex apparatus and beyond that are also not feasible under field conditions. Moreover, such methods are hazardous to health to a not inconsiderable degree because of the chemicals used, such as phenol and chloroform.

The next generation of methods for isolation of nucleic acids is based on a method for preparative and analytical purification of DNA fragments from agarose gels, developed and described for the first time by Vogelstein und Gillespie (Proc. Natl. Acad. Sci. USA, 1979, 76, 615-619). The method combines the dissolution of the agarose containing the DNA bands to be isolated in a saturated solution of a chaotropic salt (NaI), with binding of the DNA on glass particles. The DNA fixed on the glass particles is then washed with a washing solution (20 mM Tris HCl [pH 7.2]; 200 mM NaCl; 2 mM EDTA; 50% v/v ethanol) and then detached from the carrier particles. Heretofore this method has undergone a series of modifications and at present is applied for different methods of extraction and purification of nucleic acids from different sources, ultimately becoming the basis for almost all commercially available kits for manual and also automated isolation of nucleic acids. Furthermore, numerous patents and publications are now known that relate to the basic principle of isolation of nucleic acids published for the first time by Vogelstein and Gillespie, some of them containing further advantages. These variants concern both the use of different mineral carrier materials and the type of buffers used for binding the nucleic acids. Examples include the binding of nucleic acids on mineral carriers in the presence of solutions of different chaotropic salts, in which finely ground glass powder (BIO 101, La Jolla, Calif.), diatomaceous earths (Sigma Co.) or even silica gels or silica suspensions or glass-fiber filters or mineral ores (DE 41 39 664 A1; U.S. Pat. No. 5,234,809; WO-A 95/34569 DE 4321904; DE 20207793) are used as carrier materials. All of these patents are based on the binding of nucleic acids on a mineral carrier material on the basis of glass or silicon in the presence of chaotropic salt solutions. In more recent patent specifications, it is disclosed that so-called anti-chaotropic salts as components of lysing/binding buffer systems can likewise be used very efficiently and successfully for adsorption of nucleic acids on the mineral materials known to and used by the person skilled in the art (EP 1135479). In summary, the prior art may therefore be described to the effect that nucleic acids bind to mineral materials in the presence of buffers that contain chaotropic or anti-chaotropic salts or even in the presence of buffers that contain mixtures of chaotropic and anti-chaotropic salts, and in this way can then also be isolated. In this connection, preferred variants are also known in which aliphatic alcohols are additionally used for mediation of binding. It is also known to the person skilled in the art that all common commercial products for isolation and purification of nucleic acids are based on this principle. The mineral carriers used for this purpose have the form of loose bulk materials, the form of filter membranes or even the form of suspensions. Paramagnetic or magnetic particles are often used to perform automated extraction processes. Examples of these are silicate materials with a magnetic or paramagnetic core, or else iron oxide particles, the surface of which has been modified such that they have the functionalities necessary for binding nucleic acids. Modified pipette tips have been used, especially so that automated extractions can be performed more easily. These are characterized in that they already contain the carrier materials (porous mineral carrier materials or porous anion exchangers, etc.) necessary for binding nucleic acids. Thus patent specification DE3717211 describes a pipette tip with a porous chromatography material for isolation of nucleic acids. Patent specification EP1951904 discloses a pipette tip consisting of an upper and lower part, between which a porous chromatographic carrier material is likewise disposed and which is intended for use in the automated isolation of nucleic acids. A modified pipette tip for extraction of nucleic acids is also disclosed in patent specification US2013/0078619. This pipette tip also contains a porous mineral carrier material (porous glass) for direct binding of nucleic acids. It is common to all of these modified pipette tips that they contain a porous chromatographic material (loose bulk material or solid porous bodies). These carrier materials are always disposed horizontally inside the pipette tips. The liquids to be processed flow through the porous material being used. The extraction process is based on the fact that, after lysis of the sample and adjustment of necessary binding conditions for adsorption of the nucleic acids on the carrier material, this mixture is drawn by means of a pipetting process through the porous carrier material. The nucleic acids bind on the carrier material. Thereupon washing buffers are pipetted through the carrier material. Then a drying step is performed (by frequently filling and emptying the pipette or by applying vacuum). Finally, the eluent is pipetted through the carrier material. In the process, the bound nucleic acid is detached from the carrier material. The use of pipette tips containing carrier material is intended to greatly simplify the extraction of nucleic acids (especially) by an automated process. Although these ideas are already relatively old in some cases (patent specification DE3717211 dates back to 22 May 1987), such a method has not become widely accepted. The reason for this lies in some fundamental problems:

1) The pipetting of highly viscous lysates containing nucleic acids functions to only a limited extent or leads to complete clogging of the chromatographic material. Thus extraction is not possible.
2) The pipetting of lysates through a porous material causes foaming. This is intensified with the increasing number of pipetting steps and it can likewise make the extraction process impossible.

3) The removal of alcoholic components from a porous material is difficult and in many cases is not satisfactorily solved.

The object underlying the invention was therefore to solve the known problems and thus to make it possible to perform the automated extraction of nucleic acids much more easily and rapidly than heretofore. A further goal of the invention is to make it possible to use existing liquid-handling instrument platforms for automated extraction of nucleic acids. It is intended that this will be universally possible with simple means.

The object has been achieved according to the features of the claims. Claim 1 describes a device for automated extraction of nucleic acids, comprising a body that can be immersed partly or completely in a reaction cavity, wherein at least the part immersed in the reaction cavity has a rough or structured surface. It is preferable to use a corresponding pipette tip, which either has been roughened or onto which a rough or structured object has been slipped. The nucleic acids are precipitated onto this object when the polarity of the solution is lowered. This takes place preferably either by addition of an organic solvent (alcohols) or by a binding buffer known in the prior art. It has been found that binding of the nucleic acids on this object does not take place if the object has a smooth surface. Claims 2 to 6 relate to preferred embodiments of the invention.

Subject matter of the invention is also an instrument according to the walk-away principle, with which the inventive device is equipped, e.g. an automated pipetting system or an automated extraction system.

The basis of the invention is the observation that nucleic acids are adsorbed on the surface of structured or rough materials (e.g. on polymer materials). For this purpose, it is merely necessary to lyse a biological sample containing a nucleic acid, in order to liberate the nucleic acid. This can be accomplished with buffers known to the person skilled in the art. After lysis, a substance that lowers the polarity of the aqueous solution, preferably organic solvents such as alcohols or ketones, is mixed with the sample. This mixture is now brought into contact with a material characterized by a non-smooth surface. Under these conditions, nucleic acids are adsorbed on the surface of the material being used. Thereupon washing steps with known alcoholic washing solutions may be carried out. After drying, the adsorbed nucleic acid is detached from the material by addition of water or a buffer of low salt concentration (e.g. 10 mM Tris HCl), whereupon it can be used for downstream applications. The inventive device and the inventive method use this capability for a simple and automated extraction process. This device consists of a body that can be immersed partly in a reaction cavity, wherein the part immersed in this reaction cavity has a non-smooth surface. It is preferable to use a hollow body, which can receive and release liquids. A pipette tip is used particularly preferably. The pipette tip is constructed such that a structured or rough material is disposed on its outer surface in the last bottom third. This may be achieved, for example, by slipping on a fitting ring (e.g. such a ring can be slipped onto common pipette tips, thus emphasizing the universality). However, the hollow body itself may likewise have such a structural feature (roughness) and thus consist of one part and be produced in an injection-molding die. An example of the inventive device for a modified pipette tip is sketched in FIG. 1.

The invention also relates to a method for automated extraction of nucleic acids, characterized by the following steps:
a) A lysed biological sample is introduced into a reaction cavity and at least one substance that lowers the polarity of the aqueous solution or a means for binding nucleic acids on a solid phase is mixed therewith
b) A device according to one of claims 1 to 5 is immersed in this cavity, whereupon the nucleic acids bind to the rough or structured part of this device
c) If necessary, the device is transferred into at least one further cavity for washing the bound nucleic acids
d) If necessary, the bound nucleic acids are dried
e) The dried, bound nucleic acids are transferred into a further cavity for elution of the nucleic acids The term "rough surface" is to be understood as a surface that is obviously not smooth to the touch or to the eye. However, it may also be a surface that has a structure (e.g. grooves). Because of this structure, the smoothness of the surface is eliminated, even if the structure, i.e. the grooves, may itself be smooth. According to the invention, such surfaces are referred to as "structured surfaces". If it is not obvious to the eye or to the touch whether a surface is smooth or rough, a test in which a laser beam is directed onto this surface may be performed. If the surface is smooth, the laser will be reflected only in the primary direction at the surface. In the case of rough surfaces, scattering takes place in all spatial directions. Such a test has been described on the website of Kid University (http://www.tf.unikiel.de/matwis/amat/semitech_en/kap_3/illustr/oberflaechenstrukure.pdf.)

The inventive device is used with the inventive method for automated extraction of nucleic acids as follows: Preferably a traditional walk-away principle is applied, i.e. the solutions needed for extraction are introduced beforehand and successively involved in the extraction process. Corresponding to the stated goal of the present invention, even commercially available automated extraction systems or automated pipetting systems may be used for the automated extraction process, provided they meet the necessary technical criteria. The sample is introduced into a reaction cavity, then lysis buffer and if necessary proteolytic enzymes are mixed therewith. Thereupon sample lysis takes place. After lysis of the sample with known lysing buffers, an organic component is added to the lysate. The inventive device is immersed in this solution and is moved vertically up and down several times in the solution. Now the nucleic acids are disposed on this device. Thereupon the device is removed from the solution and made to move in a new reaction cavity. This contains an alcoholic washing buffer (known washing buffers may also be used for this purpose) or only an alcohol. The inventive means is immersed in this solution and is moved vertically up and down several times in the solution. The washing steps may be repeated several times. After the last washing step, the device is removed from the solution and dried briefly outside the cavity, so that the remaining alcohol is removed. In the last step, the inventive device is immersed in a further cavity, in which water or another buffer of low salt concentration is disposed. The inventive device is also immersed in this cavity and is moved vertically up and down several times in the solution. This leads to detachment of the bound nucleic acids. From this general process protocol, it is obvious how simple the automated extraction is. It is no longer necessary to separate magnetic particles, as would otherwise be the case during automated extraction by means of magnetic particles. The method does not need any vacuum-filtration steps, as are required when filter plates are used. It requires only the inventive device as well as a pipetting platform. In this connection, the universality and simplicity of the inventive device are naturally advantageous, since commercially available standard pipette tips can be used. These pipette tips are modified in such a way by slipping on a ring, for example, with the specific surface property needed for isolation of nucleic acids, that they become the inventive device and thus any appropriate pipetting platforms may be used for the isolation of nucleic acids.

Furthermore, the reagents needed for extraction may already be introduced beforehand into appropriate reaction cavities, so that the extraction process can take place according to the walk-away principle. A further particular advantage is disclosed in that the inventive means permits not only binding of the nucleic acid but furthermore is also still able to move liquids in separate ways. In this combined function, the extraction process can be still further optimized. Thus lysis of the sample can already be achieved on an automated system. The continuous movement of the sample needed for lysis is achieved by the pipetting function of the inventive device. Furthermore, after the final elution step, the eluate can also be removed from the elution cavity by means of the pipetting function and transferred into a storage vessel. Thus the degree of automation can be flexibly enhanced by this easy-to-implement double function of the inventive means.

The invention will be explained in more detail hereinafter on the basis of exemplary embodiments. These exemplary embodiments do not represent any limitation of the invention.

EXEMPLARY EMBODIMENT

Automated Extraction of Nucleic Acid from NIH 3T3 Cells by Means of the Inventive Method and Using a Modified Pipette Tin as Well as Using a Commercially Available Automated Extraction System
Variant A: Semiautomated Extraction Process (Sample Lysis Takes Place Separately)

The InnuPure C16 (Analytik Jena AG) was used as an example of a standard automated extraction system. This system is a magnetic-particle-based extraction system, which was used outside its normal purpose to perform the inventive method. At the lower end of the pipette tips used for the InnuPure C16 automated system, a ring was slipped on externally in such a way that the pipetting function was not impaired. This externally slipped-on ring consists of a polymer and has a structured surface. The combination of hollow body and ring fastened thereon forms the means for performing the inventive method.

Different quantities of NIH 3T3 cells were used for the extraction of nucleic acids. The extraction chemistry used for isolation of the nucleic acids was obtained in part from the commercial extraction kit known as innuPREP Blood DNA Kit/IPC 16X (Analytik Jena AG). Using a lysis buffer (Lysis Solution CBV) as well as Proteinase K, the cells were lysed at 60° C. for 15 minutes in a 2.0-mL reaction vessel. This lysis was not performed in the automated extraction system. Subsequently, the automated method of the Innupure C16 was used for purification of the nucleic acids. The solutions needed for extraction were present in a prefilled deep-well plate. The lysates described hereinabove were introduced into cavities filled with 400 µL isopropanol. The pipette tips equipped with the ring (the inventive means) were subjected to 80 cycles of vertical immersion movement in these cavities, each including a waiting period of 2 s at the bottom of the cavity for incubation. Then the pipette tips modified with the ring were successively immersed 10 times each in three further cavities, which contained the alcoholic washing buffer (Washing Solution LS, 80% ethanol, 80% ethanol).

Following the last washing step, the ring on the hollow body was dried for 10 minutes outside the cavity, and in this way the remaining ethanol was removed. The nucleic acids were eluted by 30 repetitions of immersion in and removal from 200 µL Elution Buffer, which had been previously adjusted to a temperature of 50° C. by the instrument. In the same cavity, a mixing step then took place by means of 80 cycles of pipetting of 100 µL at 40° C. The inventive double function of the inventive means was used for this purpose.

The method is extremely easy to perform and thereby is extremely fast. Compared with the standard method of nucleic acid extraction with the InnuPure C16 and the use of magnetic particles for binding the nucleic acids, the time savings is greater than 50%.

The isolated nucleic acid was detected by means of spectrophotometric measurement combined with gel-electrophoretic visualization in an agarose gel.

Results of the spectrophotometric measurement:

| Sample | | Concentration (ng/µL) | Yield (µg) | Ratio $A_{260}$: $A_{280}$ | Ratio $A_{260}$: $A_{230}$ |
|---|---|---|---|---|---|
| 1 | $5 \times 10^5$ NIH 3T3 cells | 72.52 | 14.5 | 1.79 | 1.53 |
| 2 | $5 \times 10^5$ NIH 3T3 cells | 64.11 | 12.8 | 1.96 | 1.58 |
| 3 | $2.5 \times 10^5$ NIH 3T3 cells | 45.19 | 9.0 | 1.74 | 1.41 |
| 4 | $2.5 \times 10^5$ NIH 3T3 cells | 32.88 | 6.8 | 1.91 | 1.29 |
| 5 | $1.25 \times 10^5$ NIH 3T3 cells | 19.4 | 3.9 | 1.8 | 1.1 |
| 6 | $1.25 \times 10^5$ NIH 3T3 cells | 10.47 | 2.1 | 1.76 | 1.05 |
| 7 | $0.62 \times 10^5$ NIH 3T3 cells | 5.65 | 1.1 | 1.34 | 0.76 |
| 8 | $0.62 \times 10^5$ NIH 3T3 cells | 5.84 | 1.2 | 1.9 | 0.7 |

As the results show, it is possible with the inventive means, solely by using standard extraction chemistry and commercially available extraction platforms, to bind and to isolate nucleic acids. It is evident that the yields are extremely high and that graduations can be observed in the yields depending on the cell quantities used.

Figure 2:
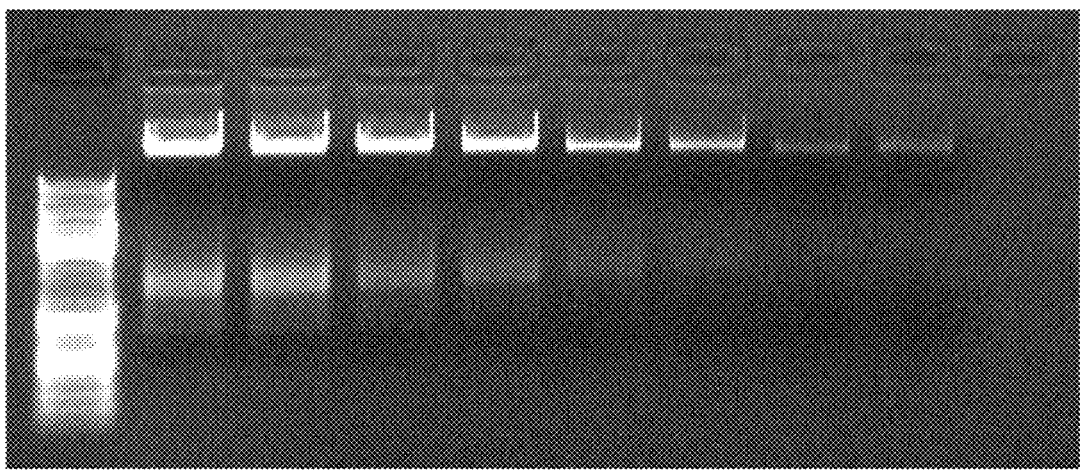

FIG. 2 shows the separation of the isolated nucleic acids by gel electrophoresis. It illustrates the nucleic acid isolated by means of the inventive method and separated electrophoretically in an 0.8% agarose gel. The samples were applied from left to right, beginning with sample 1. The applied volume was 5 µL.
Variant B: Fully Automated Extraction Process (Sample Lysis Takes Place in the Instrument)

In a further embodiment, lysis of the sample likewise takes place in an automated process. Thus only the sample and the Proteinase K must be added by the user, while the further preparation takes place by a completely automated process using the technique of the InnuPure C16. For lysis of the sample, it is heated by the Innupure C16 to 50° C., and lysis is further intensified by 250 cycles of filling and emptying of the pipette. Thereafter 400 µL isopropanol from a prefilled cavity is introduced into the cavity containing the lysate by the pipetting function of the hollow body. All further steps took place as described hereinabove.

| Sample | | Concentration (ng/µL) | Yield (µg) | Ratio $A_{260}$:$A_{280}$ | Ratio $A_{260}$:$A_{230}$ |
|---|---|---|---|---|---|
| 1 | $2.5 \times 10^5$ NIH 3T3 cells | 33.07 | 6.6 | 1.72 | 1.14 |
| 2 | $2.5 \times 10^5$ NIH 3T3 cells | 34.02 | 6.8 | 1.62 | 1.13 |

Figure 3:
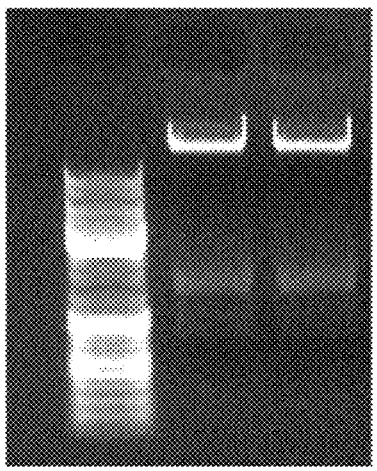

FIG. 3 shows the separation of the isolated nucleic acids by gel electrophoresis. It illustrates the nucleic acid isolated by means of the inventive method and internal lysis then separated electrophoretically in an 0.8% agarose gel. The samples were applied from left to right, beginning with sample 1. The applied volume was 5 µL.

FIG. 1 is an exemplary embodiment of the ring to be slipped onto a hollow body. The illustration is highly enlarged.

It illustrates an exemplary embodiment of the ring just as it can be used for nucleic acid extraction according to the inventive method. This shaped body with non-smooth surface can be slipped onto any appropriate commercially available pipette tips, in such a way that it is then disposed in the last bottom third of the tip.

The invention claimed is:

1. A device for automated extraction of a nucleic acid, the device comprising:
   at least one body that can be immersed partly or completely in a reaction cavity containing a nucleic acid, wherein at least a part of the at least one body immersed in the reaction cavity has a rough or structured surface,
   wherein the rough or structured surface is configured to bind to the nucleic acid during automated extraction of the nucleic acid and when the rough or structured surface is immersed in the reaction cavity, and
   wherein the at least one body comprises a smooth hollow body on which a rough or structured object is mounted externally, the rough or structured object being a ring or a sleeve mounted externally on the smooth hollow body.

2. The device according to claim 1, wherein
   the rough or structured object mounted externally on the smooth hollow body of the device is a rough or structured polymer material, a composite material with rough or structured surface or a material produced by 3D printing.

3. The device according to claim 1, wherein
   the hollow body is configured to receive a liquid disposed in the reaction cavity.

4. An instrument for automated extraction of nucleic acid, the instrument comprising:
   at least one device according to claim 1.

5. The instrument according to claim 4,
   wherein the instrument is an automated pipetting system or an automated extraction system.

6. A method for automated extraction of a nucleic acid, the method comprising:
   providing a nucleic acid in a reaction cavity;
   immersing the device according to claim 1 in the reaction cavity; and
   binding the nucleic acid on the rough or structured surface of the device.

* * * * *